(12) United States Patent
De Luca et al.

(10) Patent No.: US 9,011,607 B2
(45) Date of Patent: Apr. 21, 2015

(54) AUTOMATED MONITORING AND CONTROL OF CLEANING IN A PRODUCTION AREA

(75) Inventors: Nicholas De Luca, San Juan, PR (US); Koichi Sato, Saratoga, CA (US)

(73) Assignee: Sealed Air Corporation (US), Duncan, SC (US)

( * ) Notice: Subject to any disclaimer, the term of this patent is extended or adjusted under 35 U.S.C. 154(b) by 693 days.

(21) Appl. No.: 12/928,360

(22) Filed: Dec. 9, 2010

(65) Prior Publication Data

US 2012/0085369 A1 Apr. 12, 2012

Related U.S. Application Data

(60) Provisional application No. 61/404,683, filed on Oct. 7, 2010.

(51) Int. Cl.
| | | |
|---|---|---|
| B08B 7/04 | (2006.01) | |
| G06K 9/62 | (2006.01) | |
| G06F 19/00 | (2011.01) | |

(52) U.S. Cl.
CPC .................................. *G06F 19/327* (2013.01)

(58) Field of Classification Search
USPC .......... 134/56 R, 57 R, 18, 42; 382/100, 107, 382/143, 162, 164, 165
See application file for complete search history.

(56) References Cited

U.S. PATENT DOCUMENTS

| | | | |
|---|---|---|---|
| 5,023,597 A | 6/1991 | Salisbury | |
| 5,164,707 A | 11/1992 | Rasmussen et al. | |
| 5,305,390 A | 4/1994 | Frey et al. | |
| 5,465,115 A | 11/1995 | Conrad et al. | |
| 5,781,650 A | 7/1998 | Lobo et al. | |
| 5,973,732 A | 10/1999 | Guthrie | |
| 6,104,966 A | 8/2000 | Haagensen | |
| 6,166,729 A | 12/2000 | Acosta et al. | |
| 6,208,260 B1 | 3/2001 | West et al. | |
| 6,283,860 B1 | 9/2001 | Lyons et al. | |
| 6,392,546 B1 | 5/2002 | Smith | |
| 6,600,475 B2 | 7/2003 | Gutta et al. | |
| 6,650,242 B2 | 11/2003 | Clerk et al. | |
| 6,697,104 B1 | 2/2004 | Yakobi et al. | |
| 6,853,303 B2 | 2/2005 | Chen et al. | |
| 6,970,574 B1 * | 11/2005 | Johnson ........................ 382/100 |
| 7,015,816 B2 | 3/2006 | Wildman et al. | |
| 7,019,652 B2 | 3/2006 | Richardson | |
| 7,065,645 B2 | 6/2006 | Teicher | |
| 7,317,830 B1 | 1/2008 | Gordon | |
| 7,319,399 B2 | 1/2008 | Berg | |
| 7,375,640 B1 | 5/2008 | Plost | |
| 7,464,001 B1 | 12/2008 | Adams | |
| 7,495,569 B2 | 2/2009 | Pittz | |
| 7,534,005 B1 | 5/2009 | Buckman | |
| 7,689,465 B1 | 3/2010 | Shakes et al. | |
| 7,832,396 B2 | 11/2010 | Abernethy | |
| 8,208,681 B2 | 6/2012 | Heller et al. | |
| 8,279,277 B2 | 10/2012 | Nam et al. | |
| 2002/0190866 A1 | 12/2002 | Richardson | |
| 2003/0058111 A1 | 3/2003 | Lee et al. | |
| 2003/0061005 A1 | 3/2003 | Manegold et al. | |
| 2003/0093200 A1 | 5/2003 | Gutta et al. | |
| 2003/0163827 A1 | 8/2003 | Purpura | |
| 2003/0169906 A1 | 9/2003 | Gokturk et al. | |
| 2003/0184649 A1 | 10/2003 | Mann | |
| 2005/0027618 A1 | 2/2005 | Zucker et al. | |
| 2005/0094879 A1 | 5/2005 | Harville | |
| 2005/0134465 A1 | 6/2005 | Rice et al. | |
| 2005/0248461 A1 | 11/2005 | Lane et al. | |
| 2006/0033625 A1 | 2/2006 | Johnson et al. | |
| 2006/0219961 A1 | 10/2006 | Ross et al. | |
| 2006/0220787 A1 | 10/2006 | Turner et al. | |
| 2006/0244589 A1 | 11/2006 | Schranz | |

(Continued)

FOREIGN PATENT DOCUMENTS

| | | |
|---|---|---|
| EP | 1 939 811 A1 | 7/2008 |
| KR | 100 789 721 B1 | 1/2008 |

(Continued)

OTHER PUBLICATIONS

A. Criminisi, A. Zisserman, L. Van Gool, Bramble S., and D. Compton, "A New Approach To Obtain Height Measurements from Video", *Proc. of SPIE*, Boston, Massachussets, USA, vol. 3576, pp. 227-238 (Nov. 1-6, 1998).
A Revolution in Traceability, Foodproductiondaily.com, 1 page, (Mar. 10, 2004).
Eye in the Sky (camera), Wikipedia, 1 page (Dec. 11, 2009).
Edge Detection, Wikipedia, 8 pages (Feb. 10, 2010).
Corner Detection, Wikipedia, 12 pages (Feb. 9, 2010).
Athanasia et al, "P1714 Compliance of healthcare workers with hand hygiene rules in the emergency room of two tertiary hospitals in the area of Athens", International Journal of Antimicrobial Agents, Elsevier Science, Amsterdam, NL, vol. 29, Mar. 1, 2007, p. S486, SP022038903, ISSN: 0924-8579, DOI:DOI:10.1016/S0924-8579(07)71553-4.
Grange, Sebastian, Baur, charles: Robust Real-time 3D Detection of Obstructed Head and Hands in Indoors Environments:, J. Multimedia, vol. 1, No. 4, Jul. 2006, pp. 29-36, XP002639938, US.

(Continued)

*Primary Examiner* — Saeed T Chaudhry
(74) *Attorney, Agent, or Firm* — Schwabe, Williamson & Wyatt

(57) ABSTRACT

An automated process for monitoring and controlling cleaning in a production area comprises tracking or identifying an object the production area, monitoring the movement of fluid in the production area, analyzing the interaction between the object and the fluid to determine a level of cleanliness achieved, and triggering an event based on at least one member selected from the group consisting of: (i) the interaction between the object or body part and the fluid or fluid-like medium and (ii) the level of cleanliness achieved. The event comprises at least one member selected from generating a report, activating an alarm, report, activating an alarm, inactivating equipment in the production area, and blocking access to at least a portion of the production area. The system employing a combination of computer(s), computer vision system(s), RFID tag(s), mechanical and electromechanical, chemical, electrical, or photonic device(s) to conduct the tracking, identifying, monitoring, and triggering.

21 Claims, No Drawings

(56) References Cited

U.S. PATENT DOCUMENTS

| | | |
|---|---|---|
| 2006/0272361 A1 | 12/2006 | Snodgrass |
| 2007/0018836 A1 | 1/2007 | Richardson |
| 2007/0122005 A1 | 5/2007 | Kage et al. |
| 2008/0001763 A1 | 1/2008 | Raja et al. |
| 2008/0031838 A1* | 2/2008 | Bolling .................. 424/70.1 |
| 2008/0136649 A1 | 6/2008 | Van De Hey |
| 2008/0189142 A1 | 8/2008 | Brown et al. |
| 2008/0189783 A1 | 8/2008 | Music et al. |
| 2008/0247609 A1 | 10/2008 | Feris et al. |
| 2009/0040014 A1 | 2/2009 | Knopf et al. |
| 2009/0051545 A1 | 2/2009 | Koblasz |
| 2009/0079822 A1 | 3/2009 | Yoo et al. |
| 2009/0128311 A1 | 5/2009 | Nishimura et al. |
| 2009/0135009 A1 | 5/2009 | Little et al. |
| 2009/0161918 A1 | 6/2009 | Heller et al. |
| 2009/0195382 A1 | 8/2009 | Hall |
| 2009/0224868 A1 | 9/2009 | Liu et al. |
| 2009/0224924 A1 | 9/2009 | Thorp |
| 2009/0237499 A1 | 9/2009 | Kressel et al. |
| 2009/0273477 A1 | 11/2009 | Barnhill |
| 2010/0155416 A1 | 6/2010 | Johnson |
| 2010/0167248 A1 | 7/2010 | Ryan |
| 2010/0183218 A1 | 7/2010 | Naito et al. |
| 2010/0245554 A1 | 9/2010 | Nam et al. |
| 2011/0057799 A1 | 3/2011 | Taneff |
| 2012/0062382 A1 | 3/2012 | Taneff |
| 2012/0062725 A1 | 3/2012 | Wampler et al. |
| 2012/0146789 A1 | 6/2012 | De Luca et al. |

FOREIGN PATENT DOCUMENTS

| | | |
|---|---|---|
| WO | 99/32959 | 7/1999 |
| WO | 2007/090470 A1 | 8/2007 |
| WO | 2007/129289 A1 | 11/2007 |
| WO | 2008/152433 A1 | 12/2008 |
| WO | 2010/026581 A2 | 11/2010 |

OTHER PUBLICATIONS

United States Department of Agriculture: "Machine Vision sees food contamination we can't see", Agricultural Research Magazine, vol. 50, No. 8 Aug. 2002, XP8137410, US, retrieved from the internet: URL:http://www.ars.usda.gov/is/AR/archive/aug02/food0802.pdf {retrieved on May 31, 2011].

Bhatt J et al: "Automatic recognition of a baby gesture", Proceedings 15th IEEE International Conference on Tools with Artificial Intelligence. ICTAI 2003. Sacramento, CA, Nov. 3-5, 2003; Los Alamitos, CA, IEEE Comp. Soc, US, vol. CONF. 15, Nov. 3, 2003, pp. 610-615, XP010672284, DOI: DOI:10.1109/TAI.2003.1250248 ISBN: 978-0-7695-2038-4.

Lohr, S., "Couputers That See You and Keep Watch Over You," The New York Times, 5 pp, Jan. 1, 2011.

"GE Healthcare's Smart Patient Room to Begin Data Collection," 3 pages, Sep. 15, 2010.

U.S. Appl. No. 61/275,582, filed Sep. 1, 2009, Taneff.

* cited by examiner

AUTOMATED MONITORING AND CONTROL OF CLEANING IN A PRODUCTION AREA

This application claims the benefit of, and incorporates by reference the entirety of Provisional application No. 61/404,683 filed Oct. 7, 2010.

FIELD AND BACKGROUND

In some industries, such as the food industry and the health care industry, there is a need for workers and/or equipment in a production area to maintain a relatively high level of cleanliness. The invention is directed to automated monitoring and automated control of washing and other cleanliness-related activity in a production area.

SUMMARY

An automated process monitors and controls cleaning in a production area by tracking or identifying an object or body part in the production area, monitoring the movement, displacement, velocity profile, or transfer of a fluid (or fluid-like medium) in the production area, analyzing the interaction between the object or body part and the fluid or fluid-like medium, to determine a level of cleanliness achieved, and triggering an event based on at least one member selected from the group consisting of (i) the interaction between the object or body part and the fluid or fluid-like medium and (ii) the level of cleanliness achieved. The event comprises at least one member selected from generating a report, activating an alarm, inactivating equipment in the production area, and blocking access to at least a portion of the production area.

In an embodiment, the tracking or identifying can be carried out using a computer vision camera.

In an embodiment, the automated process can utilize an RFID tag on an object or body part, with the tracking or identifying includes sensing the presence of the RFID tag.

In an embodiment, the tracking or identifying can be carried out with equipment comprising a biometric sensor.

In an embodiment, the tracking or identifying is carried out with equipment comprising a mechanical actuator or electromechanical actuator.

In an embodiment, the displacement, velocity profile, or acceleration of the fluid is carried out with equipment comprising a computer vision camera.

In an embodiment, conductivity is measured in assessing the displacement or velocity profile or acceleration of the fluid.

In an embodiment, electromechanical means (e.g., fly wheel generator, etc.) is used to measure the displacement or velocity profile or acceleration of the fluid.

In an embodiment, chemical or pH measurements are used to determine the displacement or velocity profile or acceleration of the fluid.

In an embodiment, the report includes date and/or time.

In an embodiment, the interaction between the object or body part and the fluid or fluid-like medium is carried out using a computer vision system in combination with at least one member selected from the group consisting of a conductivity sensor, an electromechanical system, a magnetometer, an electrostatic discharge coupler, and a chemical or pH meter.

In an embodiment, the interaction between the object or body part and the fluid or fluid-like medium is carried out using an RFID tag in combination with at least one member selected from the group consisting of a computer vision system, a conductivity sensor, an electromechanical system, a magnetometer, an electrostatic discharge coupler, a chemical meter, and a pH meter.

In an embodiment, the interaction between the object or body part and the fluid or fluid-like medium is carried out using a biometric sensor in combination with at least one member selected from the group consisting of a computer vision system, a conductivity sensor, an electromechanical system, a magnetometer, an electrostatic discharge coupler, a chemical meter, and a pH meter.

In an embodiment, the interaction between the object or body part and the fluid or fluid-like medium is carried out using mechanical or electromechanical activation in combination with at least one member selected from the group consisting of a computer vision system, a conductivity sensor, an electromechanical system, a magnetometer, an electrostatic discharge coupler, a chemical meter, and a pH meter.

In an embodiment, the report is accessible on an interne web page.

In an embodiment, the report comprises a printed report.

In an embodiment, the fluid comprises at least one member selected from the group consisting of water, alcohol, acetone, petroleum distillate (e.g., oil, gasoline, mineral spirits, etc.), turpentine, steam, liquefied gas (e.g., oxygen, hydrogen, helium, nitrogen), hydrogen peroxide, salt solution, sugar solution, syrup, diluted alcohol, hypochlorous acid solution, liquefied metal, a granulated solid (e.g., ice, solid carbon dioxide, etc.), emulsified food, acetic acid solution, fluoric acid solution, carbonic acid solution, and calcium carbonate solution.

In an embodiment, the liquid comprises a dye or marker that is detectable to a camera (e.g., UV reflective material, IR reflective material, etc.).

In an embodiment, the fluid comprises soap.

In an embodiment, the liquid comprises a dye or marker that is detectable to a camera.

In an embodiment, the process further comprises triggering an event based on the assessment of the quality and/or frequency of the cleaning cycle.

DETAILED DESCRIPTION

A method for insuring that objects, body parts, or individuals ("Item") are clean and maintained in a clean state within a production environment. The system identifies and/or tracks an item using a combination of computer vision systems, RFID tags, electromechanical actuators or biometric sensors, and discerns the proximity of the item to one or multiple cleaning stations or cleaning devices. The item may engage the cleaning station to activate it or the activation may occur automatically.

Upon activation of the cleaning cycle which may also include the use of a fluid, or fluid-like cleaning "medium" which may also include a liquid or solid soap, is monitored by detecting the dispensing or velocity profile of the "medium". This may include using a computer vision system that may detect the trajectory of the medium over the item as it is dispensed. In some cases the disturbance of a fixed pool of the cleaning medium and the detection of the interference waves between the item and the cleaning medium may also be observed. In some cases the medium may be delivered as a miming stream, a vapor, a mist, a gel, through dispensers, nozzles, coding machines, thin films, as bars and the simultaneous observation of multiple mediums may be done.

As used herein, the term "fluid" includes fluid-like media, i.e., including both liquids such as water with or without the presence of soap, as well as other flowable compositions such as lotions and solid flowable granules.

As the item interacts with the medium the interaction is monitored to determine that a proper cleaning cycle has occurred. This may include the observation of how long the item was in contact with the cleaning medium, how frequently the cleaning cycle is performed, how covered the item was with the medium or soap, and how much of the medium is eventually removed from the item. Upon completion of the cleaning cycle, secondary drying processes may be performed and the detection of the level of medium removal may be observed. Once the cleaning process is completed the "item" may be tracked so as to ensure proper cleaning cycle timing or may not be tracked and only monitored when in proximity of the cleaning station. In some cases, the absence of a detection of the item may trigger secondary actions such as paging or automated interception to ensure cleaning is performed on a consistent basis. A report may thereafter be generated detailing the sequence of events or cleaning cycle characteristics.

Image data can be processed using video content analysis (VCA) techniques. For a detailed discussion of suitable VCA techniques, see, for example, Nathanael Rota and Monique Thonnat, "Video Sequence Interpretation for Visual Surveillance," in Proc. of the 3d IEEE Int'l Workshop on Visual Surveillance, 59-67, Dublin, Ireland (Jul. 1, 2000), and Jonathan Owens and Andrew Hunter, "Application in the Self-Organizing Map to Trajectory Classification," in Proc. Of the 3d IEEE Int'l Workshop on Visual Surveillance, 77-83, Dublin, Ireland (Jul. 1, 2000), both of which are hereby incorporated, in their entireties, by reference thereto.

Generally, the VCA techniques are employed to recognize various features in the images obtained by the image capture devices.

The computer system may use one or more Item Recognition Modules (IRM) to process image data for the recognition of a particular individual or other object in motion, and/or an article used in production that requires periodic leaning. In addition, the computer system may use one or more Location Recognition Module (LRM) to determine the location of a particular individual, body part, or item that requires cleaning. In addition, the computer system may use one or more Movement Recognition Modules (MRM) to process movement data for the recognition of a particular individual or other object in motion, or article. The computer may use IRM in combination with LRM and/or MRM in identifying and tracking movements of particular individual or other object in motion, or of the fluid medium for the purpose of assessing velocity of movement and/or conformational movement characteristics, as well as in assessing whether contamination control requirements are being violated. The IRM, LRM, and MRM can be configured to operate independently or in conjunction with one another.

The image data can be analyzed using human classification techniques that can be employed for the purpose of confirming whether an object is a human, as well as for analyzing the facial features. Face detection may be performed in accordance with the teachings described in, for example, International Patent WO 9932959, entitled "Method and System for Gesture Based Option Selection", and Damian Lyons and Daniel Pelletier, "A line-Scan Computer vision Algorithm for Identifying Human Body Features," Gesture '99, 85-96 France (1999), Ming-Hsuan Yand and Narendra Ahuja, "Detecting Human Faces in Color Images," Proc. of the 1998 IEEE Int'l Conf. on Image Processing (ICIP98), Vol. I, 127-130, (October 1998); and I. Haritaoglu, D. Harwood, L. Davis, Hydra: Multiple People Detection and Tracking Using Silhouettes," Computer Vision and Pattern Recognition, Second Workshop of Video Surveillance (CVPR, 1999), each of which is hereby incorporated by reference, in its entirety. Face recognition may be performed on one of the faces detected in accordance with the teachings described in, for example, Antonio Colmenarez and Thomas Huang, "Maximum Likelihood Face Detection", $2^{nd}$ Int'l Conf. on Face and Gesture Recognition, 164-169, Kilington, Vt. (Oct. 14-16, 1996), which is also incorporated by reference, in its entirety.

As used herein, the phrase "production area" refers to any area in which an automated system is used in a process of monitoring and controlling safety as individuals or machines work in an environment to make any form of measurable progress. While a typical production area would be a factory in which articles of manufacture are being produced, the phrase "production area" includes restaurants, hospitals, gas stations, construction sites, offices, hospitals, etc., i.e., anywhere a product is being produced and/or a service is being rendered. The criteria for controlling cleaning of a production area, and individuals therein, depend upon the particular nature of the production area, i.e., what articles are being produced and/or services offered, and the contamination control requirements associated with those products and/or services.

As used herein, the phrase "work zone" refers to a discrete area that can correspond with an entire production area, one or more discrete regions of a production area, or even an entire production area plus an additional area. Different regions within a production area can have different contamination control requirements. For example, a first work zone could include only a defined area immediately surrounding a particular machine in a factory. The contamination control requirements for the machine operator and others within a specified distance of the machine may be greater than the contamination control requirements just a few meters away from the machine. A factory can have many different work zones within a single production area, such as 2-100 work zones, 2-50 work zones, or 2-10 work zones. Alternatively, a factory can have uniform CCE requirements throughout the production area, which can be one single work zone.

The following examples will be provided hereafter to help further describe the invention.

Example 1

Monitoring the Washing of Hands by a Sandwich Maker in a Restaurant

In one embodiment the system can be used to monitor how frequently a sandwich maker washes their hands. Upon entering the work area each employee can be tracked using a computer vision system. A top view camera can analyze image sequences to localize the individual and individual body parts using several image features, such as (skin) color, blob shape, blob size, blob location, object motion, gradients, blob contours, histogram of oriented gradients (HOG), SIFT, and difference from background images The image of the production area and the background are obtained by taking images at fixed intervals, using low pass filtering over time:

$$B(x,y) \leftarrow \tau(x,y) + (1-\tau)I(x,y)$$

where $B(x,y)$ is background image, $I(x,y)$ is the current image, and $\tau$ is a predetermined fixed time constant.

Motion can be detected using a motion subtraction method. Motion exists if:

$$\Sigma_{(region\ of\ interest)}\{|I_n(x,y) - I_{n-T}(x,y)|\} > \text{threshold}$$

Motion detector devices can also be used.

Background subtraction can be carried out by obtaining an image of objects in the foreground, using:

$$S(x,y)=|I(x,y)-B(x,y)|>th$$

wherein S(x,y) is the foreground image (i.e., a binary image), B(x,y) is the background image, and th is a predetermined threshold value.

Body parts can also be segmented by their colors, using:

$$(c-x)^T M(c-x)<th$$

wherein "c" represents predetermined color, "x" represents pixel color to be tested, "M" represents predetermined matrix, and "th" represents a predetermined threshold.

HOG is defined by Ogale, "A Roadmap to the Integration of Early Visual Modules", IJCV Special Issue of Early Cognitive Vision, vol 72, no. 1, 9-25 (April 2007), hereby incorporated, in its entirety, by reference thereto.

Blob shape can be defined by centroid, angle, long axis, short axis of ellipse approximation, perimeter, pixel number.

SIFT is as defined by Lowe, in U.S. Pat. No. 6,711,293, which is hereby incorporated, in its entirety, by reference thereto.

Tracking the individual can be performed using a TSV transform as that described by Sato and Aggarwal in "Temporal Spatio-Velocity Transform and its Application to Tracking and Interaction", *Computer Vision and Image Understanding*, 96, pp 100-128 (2004), hereby incorporated, in its entirety, by reference thereto.

If, after an elapsed time period, which may be determined by the manager on duty, the worker has not approached the wash station (which may be pre-identified visually within an area by the computer vision system) then a reminder may be broadcast via a pager or auditory device. Another embodiment may use an RFID antenna clipped on a name tag and a reader placed near the wash station. For example, the Astra-A5-NA-POE integrated RFID reader/writer manufactured by ThingMagic, Inc, of Cambridge, Mass. When the employee approaches the sink, the system records their presence in a log file and uses this as a basis for further analysis. The secondary step involves the determination of whether the cleaning medium or soap is dispensed and whether the employee has washed their hands under the faucet for a sufficient period of time. A conductivity sensor such as a temperature sensitive faucet light water flow indicator attached to the faucet detects whether the water is flowing and this information, coupled with the verification on the vision camera that the hands of the sandwich maker are under the faucet and covered in water, provide feedback that the washing event has occurred. To determine that the worker's hands were located under the water faucet the following algorithms may be used incorporating blob analysis.

In addition a light emitting diode may be combined with the conductivity sensor and the light may be used as a marker that the computer vision system can detect. This marker may further indicate the temperature of the water; as an example red light for hot and blue light for cold. The system may catalog the water temperature used by the sandwich maker to determine the level of cleanliness achieved. A report may be generated in the following format:

| Employee Name | Duration of Handwashing (seconds) | | | Elapsed Time Between Hand Washing (minutes) | |
|---|---|---|---|---|---|
| | Min | Avg | Max | Avg | Max |
| Greg | 10.0 | 13.00 | 16.0 | 44.0 | 48.0 |
| Zack | 3.0 | 7.06 | 20.0 | 31.7 | 35.5 |
| Amelia | 4.0 | 6.75 | 15.0 | 22.6 | 25.3 |
| Becky | 4.0 | 13.20 | 26.0 | 18.5 | 21.7 |
| Brandon | 2.0 | 5.29 | 10.0 | 19.6 | 23.2 |
| Riley | 4.0 | 14.50 | 28.0 | 28.0 | 36.4 |

Example 2

Assuring that Boots are Clean in a Meat Processing Facility

In meat processing facilities it is common that a boot cleaning area be designated prior to entrance to the de-boning or meat carving area. This usually consists of a shallow 1-3 inch deep soap bath placed on the floor, through which workers are required to walk and move their feet. The solution contains chemicals that disinfect and kills germ that could migrate to the food processing area. One embodiment would use a vision system to track the approach of an individual.

Using blob analysis, features are extracted from each blob, following which the data is processed to determine whether the smallest feature distance from a model is less than a threshold value th. If the smallest feature distance is not less than the threshold value, the boot is determined to be on an individual, and further analysis can be done to determine the position of the boot in the bath.

The extraction of features from each blob is carried out by determining the long radius of the fitted ellipse, determining the short radius of fitted ellipse, determining the distance from a model contour by (a) fining the closest point in the object contour from model contour, and (b) summing the distances.

The smallest feature distance is determined by assessing the blob feature as:

$$x=(1,x_1,x_2,x_3,)^T,$$

assessing the model feature as:

$$y=(1,y_1,y_2,y_3,)^T,$$

and assessing the feature distance as:

$$d=(x-y)^T M(x-y).$$

Since there can be more than one model, find minimum of d. M is matrix, often used as inverse covariance.

Judging whether the smallest feature distance is less than the threshold value can be carried out as follows:

if $(x_1>th_1)$ and $(x_2<th_2)$ and $(x_3<th_3)$, then the boot is determined to be on. Otherwise, the boot is determined to be off.

Tracking a boot blob and maintaining stable properties of the boot-associated with the bath so that these properties can be used to make consistent determinations of whether the boot is inside or outside the bath, are carried out as follows:

Sequence breaks are found by supposing $t_0, t_1, t_2, \ldots$ are instances when a motion is detected. If $(t_{n+1}-t_n)>$threshold, then there is a sequence break between $t_{n+1}$ and $t_n$. Otherwise, $t_{n+1}$ and $t_n$ are in the same sequence. The results are grouped by sequence. Focusing on each sequence, count the number of boot OFF images (=$N_{OFF}$). If $N_{OFF}$>threshold, then output warning with image. Find a warning image in the sequence.

As the individual steps in the bath the interface between the boot and the fluid medium is detected by the camera and the system records the contact time. An indicator light can be placed ahead of the bath and activated when the proper amount of time has passed. Inappropriate shifting of boots wherein minimal fluid coverage of the boot is detected can be recorded and quickly reported. An RFID tag placed on the employee's hard hat or apron can be used to further provide additional information about the individual.

Example 3

Cleaning of Utensils in a Food Service Restaurant or a Meat Processing Plant

In both food service restaurants (such as ice cream shops, sandwich shops, or salad shops) and meat processing plants it is common for utensils to be cleaned properly between users to prevent cross contamination between foods. A strain of *E. coli* or other bacteria may be present on a particular food item or utensil and the use of knives, forks, or scoops used to cut or serve the foods can cause harm on a large scale. To prevent this, utensils should be placed in soak baths which contain low concentrations of disinfectants including acidic solutions. This may be after each use or after a specified time period. In one embodiment a utensil may be tracked by a vision camera when it is brought in contact with food items. Food can be identified by color detection and assessed as follows. First, for each pixel $p_1$=[R G B] and $p_2$=[R G B], pixel distance d is defined as $$d=(p_1-p_2)'\Sigma(p_1-p_2)$$

where $\Sigma$ is a matrix, in which inverse of covariance matrix is often used. N of pre-determined pixel sample represents food: ($s_1, s_2, s_3, \ldots, s_N$). Pixel distance ($d_1, d_2, d_3, \ldots, d_N$) is computed from each pre-determined pixel ($s_1, s_2, s_3, \ldots, s_N$). The minimum distance within N set of distances is found using: $d_{min}$=min$\{d_1, d_2, d_3, \ldots, d_N\}$. Thresholding can be carried out using a pre-determined value th. If the distance is smaller than th, the pixel is food, otherwise, the pixel is not food.

Another method of color detection, which is faster, utilizes color vector analysis wherein p=[R G B], with pre-determined vectors $a_1, a_2, a^3$, p is food pixel if $$(a_1'p<th_1) \cap (a_2'p<th_2) \cap (a_3'p<th_3) \cap$$

In determining whether the food is on or off, either of the following methods can be used. Using simple thresholding, assume features $x_1, x_2, x_3, x_4$ and predetermined threshold $th_1, th_2, th_3, th_4$, judge food as present if:

$$(x_1>th_1) \cap (x_2>th_2) \cap (x_3>th_3) \cap (x_4>th_4)$$

This may also be cross-referenced with an accelerometer and transmitter placed within the utensil or a visual marker placed on the handle of the utensil. A food item can be further detected using the vision camera and identified as a potential pathogenic source. Algorithms used to detect the food can include color based sensing. A secondary step, once the utensil has been determined to require cleaning; a proactive or training procedure may be enacted. In a proactive step, the identification of the utensil would allow the transfer of a signal that would activate a small light emitting diode on the utensil. A washing bath placed close to the employee could also have a light activated upon it to signal appropriate washing times. In a training mode, the system could record the non-compliance and create a report of the infraction and any potential foods that may have been contaminated by the occurrence.

What is claimed is:

1. An automated process for monitoring and controlling cleaning in a production area, comprising:
   (A) tracking or identifying an object or body part in the production area;
   (B) monitoring movement, displacement, velocity profile, or transfer of a fluid or fluid-like medium in the production area to determine contact between the object or body part and the fluid or fluid-like medium;
   (C) analyzing physical interactions between the object or body part and the fluid or fluid-like medium that has contacted the object or body part to determine a level of cleanliness of the object or body part that has been achieved; and
   (D) triggering an event based on at least one member selected from the group consisting of:
      (i) the physical interactions between the object or body part and the fluid or fluid-like medium and
      (ii) the level of cleanliness of the object or body part that has been achieved,
   wherein the event comprises at least one member selected from generating a report, activating an alarm, inactivating equipment in the production area, and blocking access to at least a portion of the production area.

2. The automated process according to claim 1, wherein the tracking or identifying is carried out using a computer vision camera.

3. The automated process according to claim 1, wherein an RFID tag is present on an object or body part, and the tracking or identifying includes sensing the presence of the RFID tag.

4. The automated process according to claim 1, wherein the tracking or identifying is carried out with equipment comprising a biometric sensor.

5. The automated process according to claim 1, wherein the tracking or identifying is carried out with equipment comprising a mechanical actuator or electromechanical actuator.

6. The automated process according to claim 1, wherein the displacement, velocity profile, or acceleration of the fluid is carried out with equipment comprising a computer vision camera.

7. The automated process according to claim 1, wherein conductivity is used to measure the displacement or velocity profile or acceleration of the fluid.

8. The automated process according to claim 1, wherein electromechanical means is used to measure the displacement or velocity profile or acceleration of the fluid.

9. The automated process according to claim 1, wherein chemical or pH measurements are used to determine the displacement or velocity profile or acceleration of the fluid.

10. The automated process according to claim 1, wherein the report includes date and/or time.

11. The automated process according to claim 1, wherein the interaction between the object or body part and the fluid or fluid-like medium is carried out using a computer vision system in combination with at least one member selected from the group consisting of a conductivity sensor, an electromechanical system, a magnetometer, an electrostatic discharge coupler, and a chemical meter or pH meter.

12. The automated process according to claim 1, wherein the interaction between the object or body part and the fluid or fluid-like medium is carried out using an RFID tag in combination with at least one member selected from the group consisting of a computer vision system, a conductivity sensor, an electromechanical system, a magnetometer, an electrostatic discharge coupler, a chemical meter, and a pH meter.

13. The automated process according to claim 1, wherein the interaction between the object or body part and the fluid or fluid-like medium is carried out using a biometric sensor in combination with at least one member selected from the group consisting of a computer vision system, a conductivity sensor, an electromechanical system, a magnetometer, an electrostatic discharge coupler, a chemical meter, and a pH meter.

14. The automated process according to claim 1, wherein the interaction between the object or body part and the fluid or fluid-like medium is carried out using mechanical or electromechanical activation in combination with at least one member selected from the group consisting of a computer vision system, a conductivity sensor, an electromechanical system, a magnetometer, an electrostatic discharge coupler, a chemical meter, and a pH meter.

15. The automated process according to claim 1, wherein the report is accessible on an internet web page.

16. The automated process according to claim 1, wherein the report comprises a printed report.

17. The automated process according to claim 1, wherein the fluid comprises at least one member selected from the group consisting of water, alcohol, acetone, petroleum distillate, steam, liquefied gas, hydrogen peroxide, salt solution, sugar solution, syrup, diluted alcohol, hypochlorous acid solution, liquefied metal, a granulated solid, emulsified food, acetic acid solution, fluoric acid solution, carbonic acid solution, and calcium carbonate solution.

18. The automated process according to claims 17, wherein the liquid comprises a dye or marker that is detectable to a camera.

19. The automated process according to claim 1, wherein the fluid comprises soap.

20. The automated process according to claims 19, wherein the liquid comprises a dye or marker that is detectable to a camera.

21. The automated process according to claim 1, further comprises triggering an event based on the assessment of the quality and/or frequency of the cleaning cycle.

* * * * *